(12) United States Patent
Feller

(10) Patent No.: US 8,308,349 B1
(45) Date of Patent: Nov. 13, 2012

(54) ASYMMETRIC HEAT FLUX SENSOR WITH IN-SITU DRIFT COMPENSATION

(76) Inventor: Murray F Feller, Micanopy, FL (US)

( * ) Notice: Subject to any disclaimer, the term of this patent is extended or adjusted under 35 U.S.C. 154(b) by 114 days.

(21) Appl. No.: 12/954,826

(22) Filed: Nov. 26, 2010

Related U.S. Application Data

(63) Continuation-in-part of application No. 12/941,101, filed on Nov. 8, 2010, now Pat. No. 8,132,962.

(51) Int. Cl.
*G01K 17/00* (2006.01)
*G01K 3/00* (2006.01)
*G01K 7/00* (2006.01)
(52) U.S. Cl. ............... 374/29; 374/110; 374/166
(58) Field of Classification Search .......... 374/29, 374/30, 110, 112, 166, 15
See application file for complete search history.

(56) References Cited

U.S. PATENT DOCUMENTS

| 7,736,051 B2 * | 6/2010 | Kanai et al. ............ 374/16 |
| 7,775,706 B1 * | 8/2010 | Feller ..................... 374/29 |
| 8,042,994 B1 * | 10/2011 | Feller ..................... 374/43 |
| 8,142,071 B1 * | 3/2012 | Feller ..................... 374/29 |
| 2005/0058177 A1 * | 3/2005 | Leonhardt ............. 374/16 |

* cited by examiner

*Primary Examiner* — Mirellys Jagan
(74) *Attorney, Agent, or Firm* — David Kiewit

(57) ABSTRACT

A heat flux probe uses a thermoelectric module to heat a relatively large sensing surface while cooling a substantially smaller one that is connected to the thermoelectric module by an elongated thermal conductor. A temperature difference between either the two sensing surfaces or the heated sensing surface and the cooled end plate of the thermoelectric module is controlled to have a selected value. Then the temperature change along the elongated thermal conductor is used as a measure of heat flux. This approach reduces inaccuracies arising from the thermal characteristics of the thermoelectric module and allows for in situ compensation for drift errors.

4 Claims, 2 Drawing Sheets

ASYMMETRIC HEAT FLUX SENSOR WITH IN-SITU DRIFT COMPENSATION

This application is a continuation-in-part of the inventor's U.S. Ser. No. 12/941,101, filed on Nov. 8, 2010, and issued on Mar. 13, 2012 as U.S. Pat. No. 8,132,962. The present invention deals generally with calorimetry and more specifically with apparatus and method for improving heat flux measurements.

BACKGROUND OF THE INVENTION

Background Information

Related subject matter is addressed in the inventor's U.S. patent application Ser. No. 12/941,099, filed on Nov. 8, 2010, and issued on Oct. 25, 2011 as U.S. Pat. No. 8,042,994, the disclosure of which is herein incorporated by reference.

BRIEF SUMMARY OF THE INVENTION

One aspect of the present invention is that it provides heat flux measurement apparatus comprising a thermoelectric module (TEM) having first and second end plates which are typically parallel and facing each other. The first of these end plates is thermally coupled by a first thermal conductor to a first sensing surface having a first wettable area preferably substantially larger than the area of the first end plate. The second of the end plates is thermally coupled by an elongated second thermal conductor to a second sensing surface having a wettable area preferably substantially less than the area of the second end plate. In operation of this device, the TEM is selectively electrically powered so as to heat the first end plate while cooling the second one. Temperature sensors are provided to measure the temperatures of the both sensing surfaces and of the second end plate of the TEM. This allows one to measure the temperature difference across the elongated second thermal conductor and use that temperature difference as a measure of its heat flux.

Another aspect of the invention is that it provides a method of measuring heat transfer with a fluid. This method is carried out by providing an asymmetric probe having two sensing surfaces of substantially disparate areas. Each of the sensing surfaces is coupled to a different one of the two end plates of a TEM. The probe is immersed in the fluid and the TEM is energized by an electrical power supply having a polarity chosen so that the larger of the two sensing surfaces is heated and the smaller of the two sensing surfaces is cooled. Temperature sensors embedded in the probe are used to determine the temperature difference along an elongated thermal conductor coupling one of the plates of the TEM to the smaller of the sensing surfaces and a controllable temperature difference that may be the temperature difference between the two sensing surfaces or may be the temperature difference across the TEM.

Yet another aspect of the invention is that it provides a method of calibrating a heat transfer sensor comprising a TEM coupled to two sensing surfaces having disparate surface areas, the smaller of the two sensing surfaces coupled to an associated TEM end plate though an elongated thermal conductor having a temperature sensor at each of its two ends. The sensor further comprises a temperature sensor at the larger of the two sensing surfaces. The method comprises arranging for the probe head to be in an isothermal state and then determining if there is an erroneous differential temperature signal across the elongated thermal conductor. If so, the erroneous signal is compensated for in order to re-calibrate the sensor.

Those skilled in the art will recognize that the foregoing broad summary description is not intended to list all of the features and advantages of the invention. Both the underlying ideas and the specific embodiments disclosed in the following Detailed Description may serve as a basis for alternate arrangements for carrying out the purposes of the present invention and such equivalent constructions are within the spirit and scope of the invention in its broadest form. Moreover, different embodiments of the invention may provide a variety of combinations of the recited features and advantages of the invention, and that less than all of the recited features and advantages may be provided by some embodiments.

DETAILED DESCRIPTION OF A PREFERRED EMBODIMENT

Figure 1:
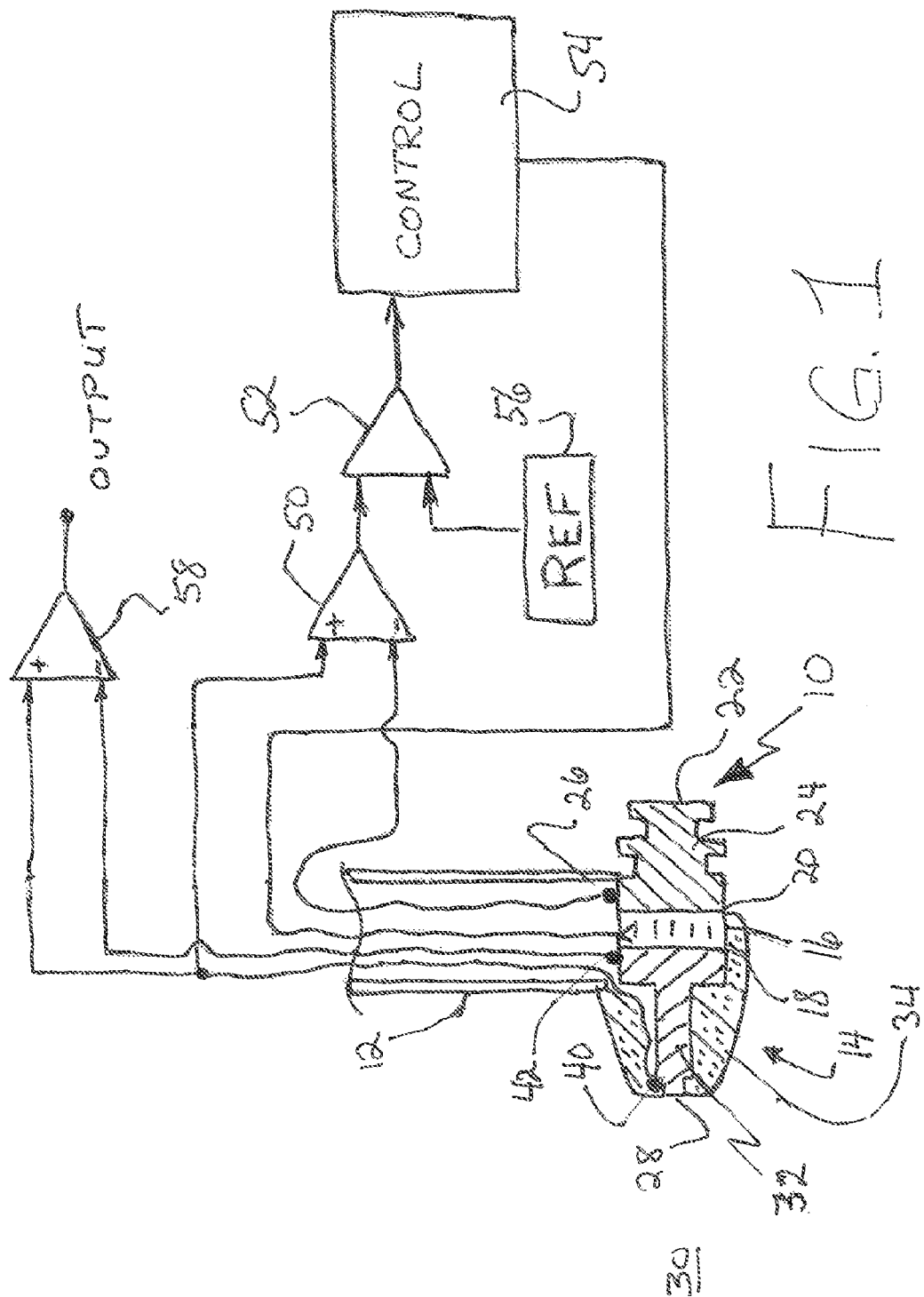
FIG. 1 is a partly schematic cross section of a preferred sensing probe and a simplified block diagram of supporting electronics.

Turning now to FIG. 1, one finds a partially schematic cross sectional depiction of a preferred heat flux sensing element of the invention 10. A partially depicted probe stem 12 is attached to a sensing head 14 preferably comprising a thermoelectric module (TEM) 16 of a known sort having a plurality of thermocouples arrayed between two alumina end plates 18, 20. Metallization patterns (not shown) on the internal facing sides of the end plates provide electrical connections to the thermocouples, which are electrically connected in series and physically arrayed parallel to each other so that when a selected DC current is passed through the TEM all of the hotter sides of the thermocouples abut one of the plates and all of the colder sides abut the other.

The end plate 20 selected to be heated in normal operation is preferably thermally coupled to a first sensing surface 22 that has, when the sensor is in use, a wetted area substantially larger than that of either end plate of the TEM. In the depicted preferred embodiment, this disparity in area is provided by thermally coupling the heated end plate 20 to a finned body 24 formed from a material that is a good thermal conductor. In the depicted embodiment a hot-end temperature sensor 26 is embedded in the finned conductor 24 to provide a measurement of the temperature of the normally heated sensing surface 22.

Correspondingly, the plate 18 selected to be cooled in operation is thermally coupled to a second sensing surface 28 that is preferably smaller than either end plate of the TEM 16. In the depicted embodiment, the cooled end plate 18 is thermally coupled to the fluid 30 by an elongated body 32 formed of a good thermal conductor embedded in a thermal insulator 34 so that heat transfer between the cold plate 18 and the fluid 30 is constrained to occur only over a small exposed sensing area 28. In the depicted embodiment two temperature sensors 40, 42 are shown in thermal contact with opposite ends of the elongated thermal conductor to provide a measure of the temperature of the smaller, normally cooled, sensing surface and of the temperature drop along the elongated body.

In a preferred embodiment, both the finned thermally conducting member 24 and the elongated thermal conducting members 32 were made of copper. The reader should understand both that many other thermal conductors may be used instead of copper and that, although many good thermal conductors are also electrical conductors, there is no requirement that the thermally coupling member be an electrical conductor.

It may be noted that although in the depicted embodiment the heated sensing surface 22 is larger than the corresponding end plate 20 and the cooled sensing surface 28 is smaller than the corresponding cooled end plate 18, neither of these constraints is required. In some applications, an external surface of the heated end plate 20 of the TEM 16 may be directly exposed to the fluid so that the associated thermal conductor 24 is unnecessary. What is required for the invention is that the wetted heated sensing area be substantially larger than the wetted cooled sensing area—e.g., preferably five times or more larger. In the depicted preferred embodiment, the areal ratio between the two sensing surfaces is on the order of 50:1 to 100:1.

When the probe is used to measure specific heat, or by extension flow rate, the TEM 16 cools the elongated conductor 32 while heating the finned conductor 24. Because the finned conductor 24 has a much larger surface exposed to the fluid, it generally has a temperature very close to that of the fluid 30, while the exposed tip 28 of the elongated conductor 32 is generally substantially colder than the fluid. Moreover, the elongated conductor 32 preferably experiences a significant heat flux-responsive temperature difference along its length when heat is transferred between the fluid 30 and the TEM 16. This temperature difference along the elongated conductor is responsive to both the specific heat and the flow rate of the fluid.

In a preferred mode of operation, a controllable temperature difference is determined by measuring the temperature signals from the temperature sensor 26 adjacent the heated surface 22 and from the temperature sensor 40 adjacent the cooled sensing surface 28. These temperature measurements are input to a differential amplifier 50 which feeds another amplifier 52 having an output to a power control and switch module 54 that regulates the power supplied to the TEM 16 in order to maintain the controllable temperature difference between the two sensing surfaces 22, 28 at a constant value irrespective of changes in ambient conditions. As is common in such circuitry, a reference signal source 56 provides an offset signal to establish the magnitude of the temperature difference.

In this preferred operating mode the TEM 16 is used only as a heat pump in a feedback control loop tightly controlled by relatively stable temperature sensors. Hence, its operating efficiency and other characteristics that are subject to change with temperature, current etc. have a smaller effect on the specific heat/flow rate measurements than is the case for other operating modes that may, for example, base the measurement on the power supplied to the TEM or on its generated voltage.

In the preferred operating mode in which the controllable temperature difference between the two sensing surfaces 22, 28 is held at a selected value, the flux-responsive temperature difference between the two ends of the elongated thermal conductor 32 extending from the cooled plate 18 of the TEM to the cooled sensing surface 28 becomes the measure of heat transfer. As depicted in FIG. 1, that temperature difference is determined by supplying the temperature signals from the sensors 40, 42 at the two ends of the elongated conductor 32 to a differential amplifier 58 which provides a specific heat/flow rate output signal essentially independent of the TEM characteristics.

In another operating mode the controllable temperature difference is selected to be the temperature difference across the TEM, as measured with the two temperature sensors 26, 42 that are adjacent the TEM. As with the previously discussed mode, the output signal is obtained from measurements from the sensors 40, 42 at the two ends of the elongated conductor 32.

Figure 2:
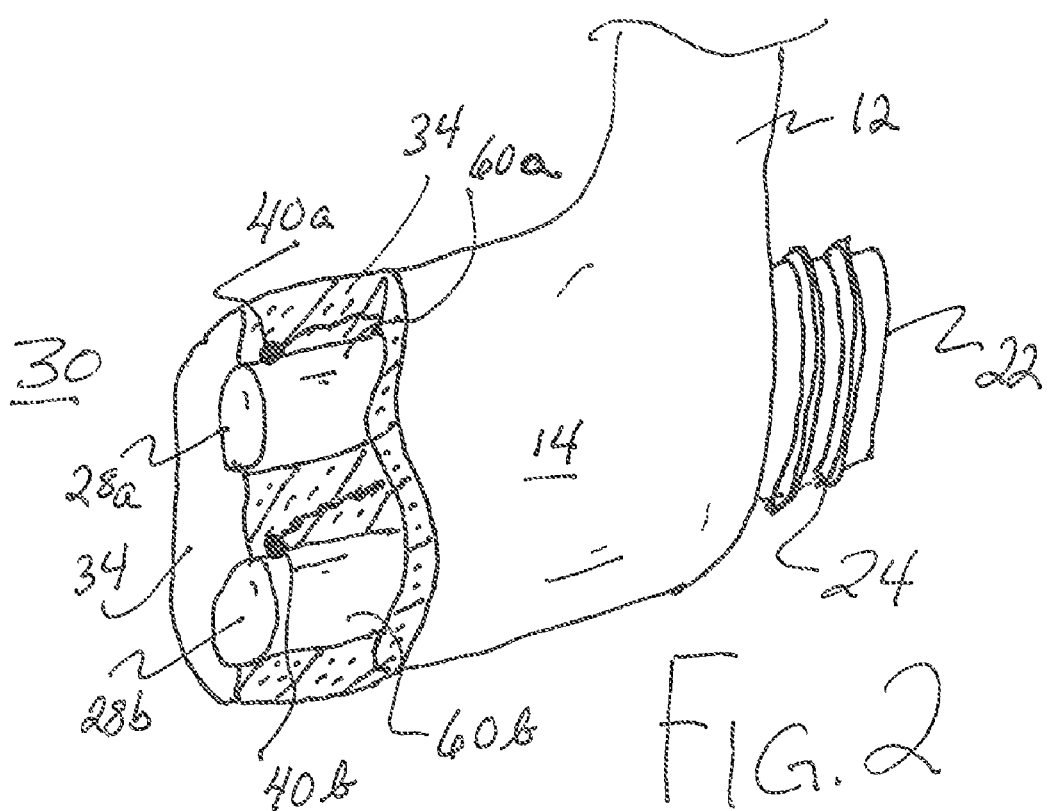
FIG. 2 is a cut-away view of an embodiment of the invention using a bifurcated thermal conductor.

Although the foregoing discussion is in terms of a probe head embodiment having a single cooled sensing surface 28, the invention is not so limited. In many flow measurement situations the rate of flow varies across the diameter of a pipe. In these cases it is desirable to measure flow at multiple points, something that can be done with an embodiment of the invention having a polyfurcated elongated thermal conductor having legs extending between a common body adjacent the cooled side 18 of a TEM 16 and each of a corresponding plurality of sensing surfaces. This is depicted in FIG. 2 for a case in which two sensing surfaces 28a, 28b are provided with associated temperature sensors 40a, 40b usable to separately measure the temperature changes along each of the bifurcated leg portions 60a, 60b of the elongated conductor. These separately measured temperature changes can then be combined (e.g., by arithmetic averaging) to determine a composite flux-responsive temperature difference.

In a sensing arrangement using a polyfurcated elongated conductor, there are several approaches to defining a composite controllable temperature difference. One approach is to combine a temperature measurement at the heated end with an arithmetic average of the temperatures of the various cooled sensing surfaces. Another approach is to combine the temperature measured at the heated end with the temperature measured at the cooled plate of the TEM. The reader will recognize that the present invention is not limited to any particular combination of temperature measurements that might be used to construct a composite controllable temperature difference or a composite flux-responsive temperature difference.

As with many other sorts of sensors, the measured output may drift over a period of time due to small changes in the temperature sensors or in the associated circuits. This can result in significant measurement errors that are of particular concern when low heat transfer rates are being measured. In most, if not all, comparable prior art systems drift compensation requires removing the sensor from the working fluid in order to recalibrate it. In the present case, because the measurement relies on temperature differences, rather than on the magnitude of some parameter (e.g., absolute temperature, transit time, etc.) the effects of drift can be compensated in situ.

The compensation method requires eliminating temperature differences across the sensing head so that all of the thermal sensors are at the same actual temperature. This can be done by de-energizing the TEM and waiting until the signals from the various temperature sensors stop changing, indicating that the sensing head has stabilized at the ambient fluid temperature. In some cases this process can be accelerated by agitating the fluid in contact with the sensor. One can also accelerate this step in the process by reversing the polarity of current supplied to the TEM for a short time so that the normally heated side is cooled and the normally cooled side is heated. In a preferred embodiment the reversed current tracks the indicated differential temperature between the two sensing surfaces provided by the temperature sensors so that it is high at the beginning and reduces as the differential temperature reduces. In another preferred embodiment the reverse current magnitude is fixed and the duration of the current tracks the differential temperature provided by the sensors.

When the probe head provides an isothermal environment, one can adjust the circuitry to compensate for the drifts, e.g., by using offset adjustments commonly provided in the amplifiers 50, 58. The reader will recognize that other approaches (e.g., using a digital processor and electronically controlled resistors) may well be preferred.

Although the present invention has been described with respect to several preferred embodiments, many modifications and alterations can be made without departing from the invention. Accordingly, it is intended that all such modifications and alterations be considered as being within the spirit and scope of the invention as defined in the attached claims.

The invention claimed is:

1. An apparatus for measuring heat flux, the apparatus comprising:
    a thermoelectric module comprising first and second end plates, the first end plate thermally coupled by means of a first thermal conductor to a first sensing surface having a first wettable area, the second end plate thermally coupled by means of an elongated second thermal conductor to a second sensing surface having a second wettable area substantially smaller than the first wettable area;
    a first temperature sensor thermally coupled to the first thermal conductor and operable to measure a temperature of the first sensing surface;
    a second temperature sensor thermally coupled to the second end plate and operable to measure a temperature thereof; and;
    a third temperature sensor coupled to the second sensing surface and operable to measure a temperature thereof.

2. The apparatus of claim 1 wherein the elongated thermal conductor is polyfurcated so as to define the second and at least a third sensing surfaces, the apparatus further comprising a fourth temperature sensor thermally coupled to the third sensing surface.

3. The apparatus of claim 1 further comprising;
    a first differential amplifier having inputs from the first and third temperature sensors and operable to provide an output representative of a temperature difference between the first and second sensing surfaces; and
    a second differential amplifier having inputs from the second and the third temperature sensor and operable to provide an output representative of a temperature difference between the second end plate and the second sensing surface.

4. The apparatus of claim 1 wherein the first wettable area is larger than the area of the first end plate and the second wettable area is smaller than the area of the second end plate.

\* \* \* \* \*